United States Patent
Carter et al.

(10) Patent No.: US 10,610,366 B2
(45) Date of Patent: Apr. 7, 2020

(54) DEMINERALIZED BONE FIBER COMPOSITION FOR USE IN MINIMALLY INVASIVE SURGERY

(71) Applicant: THERACELL, INC., Sherman Oaks, CA (US)

(72) Inventors: Andrew J. Carter, Stow, MA (US); Nelson L. Scarborough, Andover, MA (US); Oliver Scarborough, Andover, MA (US)

(73) Assignee: Theracell, Inc., Sherman Oaks, CA (US)

( * ) Notice: Subject to any disclaimer, the term of this patent is extended or adjusted under 35 U.S.C. 154(b) by 0 days.

(21) Appl. No.: 15/546,856

(22) PCT Filed: Jan. 29, 2016

(86) PCT No.: PCT/US2016/015845
§ 371 (c)(1),
(2) Date: Jul. 27, 2017

(87) PCT Pub. No.: WO2016/123583
PCT Pub. Date: Aug. 4, 2016

(65) Prior Publication Data
US 2018/0000595 A1 Jan. 4, 2018

Related U.S. Application Data

(60) Provisional application No. 62/109,549, filed on Jan. 29, 2015.

(51) Int. Cl.
*A61F 2/30* (2006.01)
*A61F 2/28* (2006.01)
(Continued)

(52) U.S. Cl.
CPC ............ *A61F 2/30965* (2013.01); *A61F 2/28* (2013.01); *A61F 2/3094* (2013.01);
(Continued)

(58) Field of Classification Search
CPC .................................. A61L 27/36; A61F 13/00
See application file for complete search history.

(56) References Cited

U.S. PATENT DOCUMENTS

| 4,348,377 A | 9/1982 | Felder et al. |
| 4,639,366 A | 1/1987 | Heller |

(Continued)

FOREIGN PATENT DOCUMENTS

| EP | 0 023 992 A1 | 2/1981 |
| EP | 0 168 277 A1 | 1/1986 |

(Continued)

*Primary Examiner* — Yashita Sharma
(74) *Attorney, Agent, or Firm* — Umberg Zipser LLP

(57) ABSTRACT

A bone repair composition and methods thereof include bone fibers made from cortical bone in which a plurality of bone fibers are made into various implant shapes conducive to introduction into a patient through minimally invasive surgery. The bone fiber compositions may be in the form of a pellet or cylinder. A method includes producing the bone fiber graft efficiently with control of key parameters of cohesiveness, rehydration and swelling of the bone fiber graft. Another method includes introducing the bone fiber graft into the cannula efficiently. A method is also provided to allow introduction of a bone graft into a patient by placing the implant in a tube and expelling it through the action of a plunger.

6 Claims, 3 Drawing Sheets

(51) Int. Cl.
*A61L 27/36* (2006.01)
*A61F 2/46* (2006.01)

(52) U.S. Cl.
CPC .......... *A61F 2/4601* (2013.01); *A61L 27/365* (2013.01); *A61L 27/3608* (2013.01); *A61F 2002/2835* (2013.01); *A61F 2002/4627* (2013.01); *A61L 2430/02* (2013.01)

(56) References Cited

U.S. PATENT DOCUMENTS

| | | |
|---|---|---|
| 4,764,364 A | 8/1988 | Heller et al. |
| 4,765,973 A | 8/1988 | Heller |
| 4,877,864 A | 10/1989 | Wang et al. |
| 5,013,649 A | 5/1991 | Wang et al. |
| 5,106,748 A | 4/1992 | Wozney et al. |
| 5,108,922 A | 4/1992 | Wang et al. |
| 5,116,738 A | 5/1992 | Wang et al. |
| 5,366,875 A | 11/1994 | Wozney et al. |
| 5,447,711 A | 9/1995 | Almen et al. |
| 5,695,742 A | 12/1997 | Felder et al. |
| 6,294,187 B1* | 9/2001 | Boyce ................ A61F 2/28 424/422 |
| 6,616,698 B2 | 9/2003 | Scarborough |
| 6,630,153 B2 | 10/2003 | Long et al. |
| 8,663,672 B2 | 3/2014 | Manrique et al. |
| 2005/0105385 A1* | 5/2005 | McGill ............ A61B 17/8805 366/139 |
| 2008/0065088 A1* | 3/2008 | Hughes ............. B01F 5/0685 606/93 |
| 2010/0256774 A1 | 10/2010 | Wang et al. |
| 2012/0245703 A1 | 9/2012 | Meredith |
| 2014/0314822 A1 | 10/2014 | Carter et al. |

FOREIGN PATENT DOCUMENTS

| | | |
|---|---|---|
| EP | 0 177 414 A1 | 4/1986 |
| EP | 0 308 364 A2 | 3/1989 |
| WO | WO 85/01727 A1 | 4/1985 |
| WO | WO 92/08691 A1 | 5/1992 |
| WO | WO 93/00432 A1 | 1/1993 |
| WO | WO 94/26892 A1 | 11/1994 |
| WO | WO 94/26893 A1 | 11/1994 |

* cited by examiner

DEMINERALIZED BONE FIBER COMPOSITION FOR USE IN MINIMALLY INVASIVE SURGERY

CROSS-REFERENCE TO RELATED APPLICATION(S)

This application is a National Phase Patent Application and claims priority to and the benefit of International Application Number PCT/US2016/015845, filed on Jan. 29, 2016, which claims priority to and the benefit of U.S. Provisional Patent Application No. 62/109,549, filed on Jan. 29, 2015, the entire contents of all of which are incorporated herein by reference.

INTRODUCTION

Bone grafts are commonly used to treat defects in the skeletal system caused by injury or disease. Skeletal defects often require bone grafts to maintain space and provide a matrix for healing. A graft should provide or facilitate the various mechanisms of bone healing including osteoconduction, osteoinduction, and osteogenesis. Osteoconduction is the ability of the graft to act as a matrix or scaffold to support bone formation. Osteoinduction is a result of bone growth factors that stimulate differentiation of local cells to become bone forming cells, i.e. osteoblasts. Bone morphogenic proteins (BMP's) that are naturally occurring in bone, or that may be produced by recombinant gene technologies, are responsible for osteoinduction. Osteogenesis refers to the formation of bone, and may also be used to reference the ability of cells, to form bone. Bone forming cells may either be resident at the graft site or transplanted to the site by autogenous bone, bone marrow aspirate and/or cell implantation. Considering these requirements to form bone, a need exists for a reproducible and cost-effective process of making a bone graft having improved osteoconductive and osteoinductive properties.

A further issue with the use of demineralized bone fiber (DBF™) grafting materials is providing the material in a form that facilitates easy surgical introduction into the patient. For many procedures, the size of the incision may be minimized to reduce the surgical trauma and patient recovery time. This requires that the graft be delivered through relatively long (15-30 cm) cannulae of small diameter (3-15 mm).

DETAILED DESCRIPTION

Figure 1A:
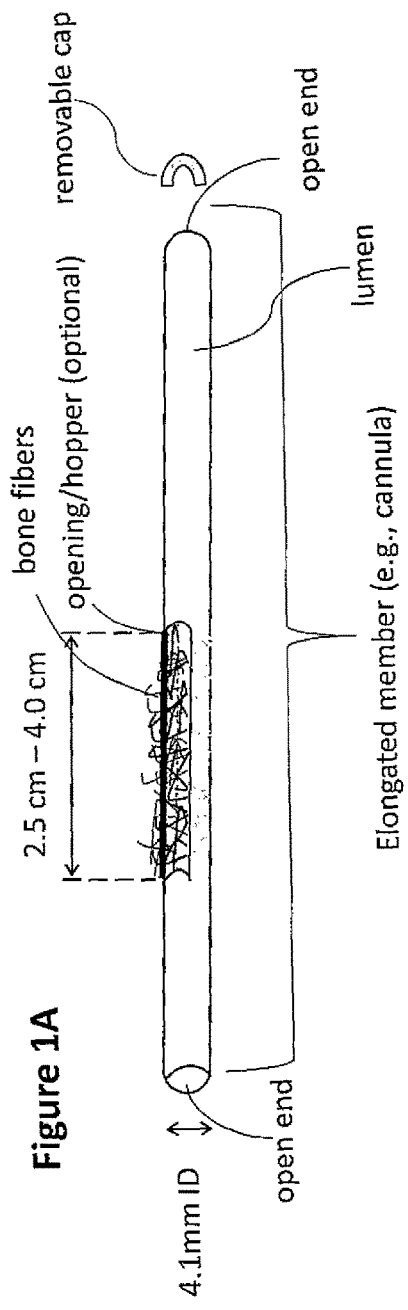
FIG. 1A shows a device for forming bone repair implants from bone fibers, according to embodiments of the present invention.

With the continued innovation in minimally invasive surgery for orthopedic and spine procedures a need has arisen to be able to efficiently and accurately place bone grafts into defects deep within a patient's body with minimal access due to small incisions. Long, small diameter tubes are used to provide a route for surgical instruments to be guided to the targeted site being operated on. This situation makes it difficult to place bone grafts. There are significant challenges with the currently available bone graft options. When one attempts to deliver bone graft (e.g. autograft, Demineralized Bone Matrix (DBM), or stem cell products with bone matrix) through cannulae it may bind within the cannulae making it difficult and frustrating for the surgeon. Inserting the graft into the tube is challenging and when the plunger or push rod or other transporting mechanism is then inserted to advance the graft, the graft may bind within the cannula. This problem occurs with all of the currently available graft materials creating a problem that has not been solved prior to the technology described in this disclosure. Embodiments of the present invention include a device to form pellets of graft materials as well as control the rehydration rate, the extent of swelling during rehydration and deliver the graft material sequentially through long cannulae of various inner diameters for a more efficient and controlled process.

The binding of the graft material to the cannulae may be caused by several problems. One reason is that the space between the rod and inner diameter of the cannulae tubes allows for material to be positioned between the plunger and cannula wall during the plunging or advancing step causing friction and binding. Another reason is due to a process known as granular mechanics where particulate material under pressure becomes extremely hard. This property of granular materials is well known and is used in construction where materials such as sand or gravel are sorted to provide relative uniformity.

The difficulty in delivering bone graft through tubes has several consequences. One is that the graft has to be placed in very small quantities sequentially until adequate volume is achieved. The other is that the additional manipulation and time required accomplishing this increases costs and risks of the surgical procedure. Further, having to exert force to advance the graft opens the possibility of the pushing mechanism to be over advanced and damage tissue within the site causing patient injury. Embodiments of the present invention overcomes this problem using a straightforward approach including a lubricious bone fiber composition, a method of making the lubricious bone fiber pellet composition, a device for forming the bone fiber pellet composition, a device for holding or storing a plurality of bone fiber pellets, and an apparatus for delivering a bone fiber pellet to a subject using minimally invasive surgery (MIS).

As used herein, "demineralized bone fiber" (DBF), "bone fiber pellet," "bone fiber implant," "bone implant," "implant," "graft," "DBF pellet," "DBF implant," and like terms refer to a composition of compressed bone fibers for implant into a subject by any surgical means, including minimally invasive methods.

As used herein, 'annealing', 'hardening' and like terms refer to the effect of heating the graft to form intermolecular bonds of collagen for 'cross-links' between collagen molecules. This may be controlled to only occur at the outermost layer of bone fibers.

As used herein, an "elongated member" is not limited to any particular cross sectional shape. An example of an elongated member includes a tube, such as a cannula.

The problem of being able to advance the bone graft through narrow tubes has been overcome by developing a graft material such that the issue of granular mechanics is overcome. The bone graft form according to embodiments of the present invention uses bone which has had the mineral component removed by a demineralization process which renders the graft malleable and not hard. The bone is then further formed into fibers by cutting along the long axis such that the collagen fibers within it are maintained in their natural fibrous form. This material may then be placed into tubes for delivery.

At this stage, if the demineralized bone fibers (DBF) are pushed through the tube they may be advanced, but the possibility of binding between the tube and rod may still occur due to fibers becoming interposed between the push rod and the inner lumen of the cannula. A further step according to embodiments of the present invention includes forming the fibers into pellets such that they are coherent and do not have a tendency to become separated and get stuck into this space. The property of the DBFs to form a coherent mass makes them particularly amenable to this application. Fibers are placed into a mold and compressed—either isotropically, uniaxially, horizontally, or vertically. In one method, fibers are placed into a tube, the opening is covered and the fiber-based graft material is compressed using a plunger. The resulting pre-compacted fiber pellets now take a form analogous to pledgets, i.e. discrete, formed solids which are compressible but do not exhibit granular mechanical properties. This form of graft does not allow for material to become interposed between the rod and tube and thus the graft may be readily advanced without binding.

A further refinement and feature of embodiments of the present invention is an additional and optional step in the process in which the DBF material is heated. Heating the DBF to between about 40° and 70° C. for a period of 1 min to 300 min to anneal it increases the coherency of the DBF. In some embodiments heating of the DBF is carried out at a temperature between about 45° and 65° C. or between about 45° and 65° C. This is due to the collagen component undergoing reversible denaturation where the triple helix of the collagen molecules unwind slightly, and then when cooled back toward body temperature, 37° C., the intermolecular hydrogen bonds tend to reform, but to adjacent molecules such that crosslinking occurs. This natural process of forming crosslinking makes it so the collagen fibers form a more interconnected architecture.

The other aspect of the heating process according to embodiments of the present invention is that it may be done in a manner that concentrates the crosslinking on the surface of the implant to further maintain the shape of the pellet. This surface annealing may be achieved by placing the implant in a heat conductive tube or mold during the heating process. In some embodiments, the heat conductive tube or mold is metallic. In some embodiments, the heat conductive tube or mold is made from stainless steel. The heat conductive nature of the mold provides an annealed outer layer (e.g. a seared outer layer) on the pellet, making the pellet smooth and lubricious such that advancing through a tube is further facilitated. The heating process may be finely controlled to allow properties to be dialed in with great specificity. The surface hardening process may be finely controlled to not compromise the porosity of the implant and hence does not interfere with the rehydration of the implant, or with tissue ingrowth while enhancing integrity for placement through a cannula.

An alternative method for maintaining cohesiveness of the graft is to use chemical crosslinking agents such as glutaraldehyde, bis-carbodiimide, water-soluble epoxy crosslinking agents such as 1,4-butanediol diglycidyl ether (BDDGE), diisocyanates, divinyl sulfone (VS), 1,4-butanediol diglycidyl ether (BDDE), ultraviolet radiation, gamma radiation, electron beam radiation, formation of formation of an acyl azides, or other crosslinking agents and methods known in the art. By controlling the process, crosslinking may be limited to the surface layer of the implant in a manner analogous to the annealing process as described in this disclosure.

A desirable property which has not been previously described or recognized in the art is that in addition to helping hold the shape and adding lubricity, once the graft is placed into the site the surface hardening or annealing maintains the graft in the discrete shape, but if properly done then readily allows rehydration by body fluids and as this occurs allows the graft to swell and fill the void. This property of being able to insert a small graft that then swells and fills the space is of great utility for several reasons. One, it allows for efficient delivery to the site in that a small volume expands to fill a large volume. Two, for bone to form and fill voids it needs a matrix. Bone fills holes poorly without a matrix and this is why grafting is performed. If the graft does not completely fill the defect, the voids will remain. This is why fractures must be reduced to close the gap and if this is not done it leads to nonunion and delayed unions. In the case of comminuted fractures that cannot be completely reduced grafting is required. In MIS procedures getting adequate graft to fill the site and provide complete graft host contact is particularly difficult and risky. If this occurs it is not readily detectable due to limited visualization.

The ability to vary and control the degree of surface hardening by the heating process is a component of embodiments of the present invention and improves the utility of the graft.

In some embodiments, the methods for making the bone fibers include demineralizing whole bone and subsequently cutting the demineralized bone in a direction parallel to the orientation of collagen fibers within the demineralized bone to form elongated bone fibers. The bone material according to embodiments of the present invention is derived from human (allograft) or animal (xenograft) cortical bone and is processed in such a manner to provide grafts of high utility based on the controlled geometry of the bone fibers. For veterinary applications bone from the same species—i.e. canine for canine patients (allograft) may be used as well as bone from other species (xenograft). It will be obvious to one skilled in the art that fibers other than demineralized bone fibers may be utilized to make a bone graft according to embodiments of the present invention. Such fibers may be made from resorbable polymers, or bioactive glasses or mixtures thereof, and could be used in place of, or as an additive to the demineralized bone fibers. The methods of preparation of the graft provide improved efficiency and uniformity with reproducible results and decreased requirements for equipment and resulting costs. The bone graft forms according to embodiments of the present invention do not require the addition of exogenous materials to maintain the form of the graft. These improved characteristics will become apparent to one skilled in the art based upon the present disclosure.

Processing of Fibers. Processing of the demineralized bone fibers to produce a desired shape or form of the bone fibers may be performed using any suitable method. Examples of bone fiber products according to embodiments of the present invention include, but are not limited to: a pellet, bullet, cone and a cylinder. To make some of these forms, the bone fibers may be collected and compressed using pressure molds. In some embodiments, the bone fibers are formed using a wet lay technique as is well understood by those skilled in the art of nonwoven or paper manufacture. Using a wet lay technique, the cut bone fibers are suspended in an aqueous solution to form a bone fiber slurry. Any suitable biocompatible aqueous solution may be used. Non-limiting examples of biocompatible aqueous solutions include: water, saline, and/or solutions including salts such as Ringer's solution, Lactated Ringer's solution, and saline with 5% dextrose. In some embodiments of the present invention, cut fibers are placed into saline to create a slurry of entangled bone fibers. The bone fiber slurry is suspended over a mesh screen and the saline is drained resulting in a wet lay process, such that a sheet of demineralized bone fibers is formed on the mesh screen. The thickness of the sheet depends on the amount of fibers and the size of the mesh screen. The resulting fiber sheet may be then dried using heat and/or vacuum or other means such as lyophilization (freeze-drying). In some embodiments of the present invention, prior to drying, the sheet is placed in a mold and compressed to a defined thickness and shape, followed by drying. Alternatively the sheet may be rolled or wrapped. Following drying the sheet or form derived from the sheet may be cut into pellets. As discussed herein, density, porosity and overall dimensions of the resulting product may be controlled using various molds and techniques.

In some embodiments the screen may itself be contoured to provide a three dimensional shape to the screen such that pellets may be directly produced.

Fibers may also be placed into a mold cavity and compressed using a plunger or push rod.

In some embodiments, the formed wet lay fiber forms may be placed into an oven and heated as a means to enhance cohesiveness of the bone fiber product. As used herein, "cohesive" and "cohesiveness" are used to refer to the integrity of the bone fiber products. That is, a cohesive bone fiber product stays together, does not fall apart and maintains its shape. As the bone fibers are in a hydrated state, heating to temperatures of about 30 to about 70° C., or, for example, 45-55° C. for about 1 minute up to about 3 hours increases the cohesiveness by increasing the adherence of the collagen to other strands, i.e. annealing or hardening.

In some embodiments a vacuum oven is used whereby the application of vacuum removes moisture and dries the implant. In some embodiments, the process of heating and applying a vacuum includes dehydrothermal treatment as described in Scarborough, U.S. Pat. No. 6,616,698.

In some embodiments the heating step is undertaken by placing the implant in contact with a metal or other high heat-conductivity surface such that the degree of annealing/crosslinking is enhanced at that surface.

In some embodiments the implant has a domed or tapered end, or is pellet shape to facilitate subsequent introduction into the delivery system. Shaping the pellet so that the front tip is convex and rear end concave may be beneficial. This may be accomplished by shaping the holder cover, push rod and interfaces accordingly.

In other embodiments, the bone fibers are further processed in a second drying step that may include vacuum drying and/or lyophilization.

In other embodiments the bone fibers may retain some moisture and may be placed in moisture impervious packaging.

In some embodiments the amount of compression, heating, and drying may be tailored to modify the rehydration and re-expansion rates. For example with no heating, the rehydration is fast, whereas heating at 55° C. for approximately one hour causes very slow re-hydration and re-expansion. By altering these processes, bone fiber compositions according to embodiments of the present invention may retain their manufactured shape during packaging, shipment, unpacking and placement into the graft site, and then after placement into the graft site the DBF will begin to absorb moisture rapidly (within 30 seconds or less) and may be completely re-hydrated/re-expanded within approximately 2 minutes, and may be completely re-hydrated/re-expanded within 30 seconds. Alternatively, the rehydration of the DBF may be slow.

The ability of the parameters of various stages of the above process to be modified allow for a broad range of products to be produced. A non-limiting range of bone fiber products includes cylinders, pellets, and cones, all of which may be used to fill voids wherever bone formation is required. Example indications that may utilize such an implant product include spine, trauma, dental, craniofacial, and oral maxillofacial surgery.

In some embodiments, bone fiber pellets are formed by adding wet fibers directly into a cylindrical mold. An example of a cylindrical mold is a metal tube. A bone fiber pellet shape is useful as it may be delivered to a graft site using a cannula as commonly used for minimally invasive surgery. The bone fiber pellets are capable of passing through a tube. A cylindrical mold is loaded with the fiber. A tamp is used to apply some compression to the fibers. In some embodiments, a fiber loaded cylindrical mold is dried by heat, vacuum, and/or lyophilization. After drying, the bone fiber pellet becomes more cohesive and shrinks to a reduced volume. After drying, the bone fiber pellets may be easily expelled out of the mold due to the shrinkage that occurs upon drying. The bone fiber pellets may be subsequently introduced into a liquid, such as water, saline, blood, and/or bone marrow aspirate, and they are readily rehydrated and expanded. After placement into surgical sites, rehydration occurs naturally due to the resident blood and moisture within the site. In some embodiments, one or more such bone fiber pellets may be utilized for minimally invasive grafting procedures such as spinal fusion, trauma and bone cysts as examples.

While wet lay techniques may be used for the manufacture of different shapes from the bone fibers, it will be recognized that any other molding or forming technique used with textile fibers could be used. Fibers with and without excipients may be directly molded using compression into any shape. In some embodiments excipients may be selected that enhance the lubricity of the implant facilitating delivery and further reducing and friction or binding during this procedure.

Entanglement of the fibers may be increased by placing fibers between rollers and rolling, such as may be achieved using a cigarette roller. Equipment using the same design as a cigarette roller may be used to produce implants according to embodiments of the present invention.

Alternatively, entanglement may be increased by stirring the fibers while in a liquid slurry. By creating a vortex fibers are swirled and induced to become entangled. This results in non-woven 'ropes' of fibers that may then be cut to length and processed into pellets as described within this disclosure.

It is important that the implants are able to swell post implantation so that they are substantially space-filling. This is achieved by careful control of the processing conditions such as the optional compression of the fibers and the optional heating and optional drying steps.

Excipients and Additives. The ability of the demineralized bone fiber products to mix with autograft bone, bone marrow aspirate and other materials improves the surgical utility of an implant made from the demineralized bone fibers according to embodiments of the present invention. Various aspects of product design including density, porosity, etc. influence the mixability and handling and may be incorporated into the design to maximize these properties. The ability to control the geometry of the demineralized bone fiber particles allows for tailoring the product for the indication.

In some embodiments of the present invention, incorporation of excipients may enhance handling properties of the bone graft and or ease of manipulation through the elongated member (e.g., tube or cannula). An excipient may be added to the bone material subsequent to demineralization. That is, an excipient may be added to the bone material before, after or concurrently with the bone cutting. Non-limiting examples of excipients that are also referred to as swelling agents, include liquid polyhydroxy compounds and liquid polyhydroxy compound derivatives. The polyhydroxy compounds and derivatives of this type include those which in the pure or concentrated state and at ambient temperature are normally solid or semi-solid but are soluble in a suitable solvent, e.g., water, physiological saline, ethanol, glycerol, glucose, propylene glycol, polyethylene glycol of from 200-1000 molecular weight, etc., or mixtures thereof, to provide a liquid composition.

In particular, useful polyhydroxy swelling agents possess from 2 to about 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives thereof. Specific polyhydroxy compounds include ethylene glycol, diethylene glycol, triethylene glycol, 1,2-propanediol, trimethylolethane, trimethylopropane, erythritol, pentaerythritol, polyalkylene glycols such as the polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, trehalose, carrageenan, agar, alginic acid, guar gum, gum tragacanth, locust bean gum, gum arabic, xanthan gum, amylose, mixtures and copolymers thereof.

Derivatives of the polyhydroxy compounds, in particular, ester derivatives thereof, are also useful as swelling agents. For example, liquid and solid monoesters and diesters of glycerol may be used to good effect, the solid esters being dissolved up to the limit of their solubility in a suitable vehicle, e.g., propylene glycol, glycerol, polyethylene glycol of 200-1000 molecular weight. Liquid glycerol esters include monacetin and diacetin and solid glycerol esters include such fatty acid monoesters of glycerol as glycerol monolaurate, glyceryl monopalmitate, glyceryl monostearate, etc. An example of a carrier herein comprises glyceryl monolaurate dissolved in glycerol or a 4:1 to 1:4 mixture of glycerol and propylene glycol.

In some embodiments, polyhydroxy excipients include glycerol and its liquid monoesters and diesters, e.g., monacetin and diacetin, fructose, trehalose, glucose and sucrose, and mixtures thereof. Where the polyhydroxy compound is a solid, e.g., sucrose, a solvent such as water, glycerol, polyethylene glycol of from 200-1000 average molecular weight, or mixture thereof is used to provide a flowable solution or bone fiber putty.

Additional non-limiting examples of suitable excipients include: lecithin, polyoxamer, hyaluronic acid, alginate, derivatized hyaluronic acids, and modified celluloses including carboxyl methyl cellulose and hydroxypropyl cellulose.

In some embodiments excipients are selected that enhance the lubricity of the implant and facilitate delivery through cannulae by reducing friction. Excipients such as biocompatible fats and oils, surfactants, etc. are particularly amenable to this functionality.

In some embodiments, a biocompatible material (an additive) is included to enhance the osteogenic properties of the bone implant. In some embodiments of the present invention, the bone fiber composition may also include an additive selected from bone marrow cells, mesenchymal stem cells, oxygenating materials (i.e., oxygen carrying materials), oxygen generating compounds, growth factors, antibiotics, antineoplastic agents, or combinations thereof. In some embodiments, the bone repair composition includes oxygenating materials such as a perfluorocarbon (PFC). In some embodiments, the repair composition includes oxygen generating compounds such as peroxides (e.g., hydrogen peroxide, calcium peroxide), perchlorates (e.g., sodium perchlorate, potassium perchlorate) percarbonates (e.g., sodium percarbonate), or perborates (e.g., sodium perborate).

The addition and selection of at least one biocompatible material may depend on the size of the bone graft site and the location of the site. Additional examples of biocompatible materials include: collagen and insoluble collagen derivatives, hydroxyapatite, tricalcium phosphate, and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin; amino acids, magainins, peptides, vitamins, inorganic elements, co-factors for protein synthesis; hormones; endocrine tissue or tissue fragments; synthesizers; enzymes such as collagenase, peptidases, and oxidases; polymer cell scaffolds with parenchymal cells; surface cell antigen eliminators; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; nucleic acids; and, bioerodable polymers such as those disclosed in U.S. Pat. Nos. 4,764,364 and 4,765,973 and European Patent Application 168,277. The amounts of such optionally added substances may vary widely with optimum levels being readily determined in a specific case by routine experimentation.

Other additives are contemplated to modify biological or other properties according to embodiments of the present invention. Non-limiting examples include growth factors such as bone morphogenetic proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-.betas), including TGF-.beta.-1, TGF-.beta.-2, and TGF-.beta.-3, and inhibitors for tumor necrosis factor (e.g., anti-TNF-alpha.). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, the entire contents of which is incorporated herein by reference. The polynucleotides encoding the same may also be administered as gene therapy agents. Example bioactive substances include the recombinant human bone morphogenetic proteins (rhBMPs) because they are available in relatively unlimited supply and do not transmit infectious diseases. In some embodiments, the bone morphogenetic protein is a rhBMP-2, rhBMP-4, rhBMP-7, or heterodimers thereof. BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al., the entire contents of all of which are herein incorporated by reference.

In some embodiments of this invention additives that improve the x-ray opacity of the implant may be utilized. Suitable conventional water soluble non-ionic X-ray contrast agents are iodinated aromatic compounds, which have one or several aromatic nuclei that are at least triiodo-substituted. Such agents are shown in U.S. Pat. No. 5,695,742 and comprise CAS (Chemical Abstract Service) registration numbers 31112-62-6 (metrizamide), 60166-93-0 (iopamidol), 78649-41-9 (iomeprol), 73334-07-3 (iopromide), 877771-40-2 (ioversol), 66108-95-0 (iohexol), 89797-00-2 (iopentol), 107793-72-6 (ioxilan), 99139-49-8 (11-1), 75751-89-2 (iogulamide), 63941-73-1 (ioglucol), 63941-74-2 (iogulucamide), 56562-79-9 (ioglunide), 76984-84-0 (MP-7011), 64965-50-0 (MP-7012), 77111-65-0 (MP-10007), 79944-49-3 (VA-7-88), 79944-51-7 (also shown in EP 033426), 79211-10-2 (iosimide), 79211-34-0 (iocibidol), 103876-29-5 (also shown in EP 0177414), 141660-63-1 (iofratol), 92339-11-2 (iodixanol), 79770-24-4 (iotrol), 71767-13-0 (iotasul), 81045-33-2 (iodecol), 143200-04-8 (also shown in WO 92/08691), 143199-77-3 (also shown in WO 92/08691), 143200-00-4 (also shown in WO 92/08691), 78341-84-1 (also shown in U.S. Pat. No. 4,348,377), 122731-47-9 (also shown in EP 0308364), 122731-49-1 (also shown in EP 0308364), 99139-65-8 (also shown in WO 85/01727), 99139-62-5 (also shown in WO 85/01727), and 78341-84-1 (also shown in EP 0023992).

Other such water soluble non-ionic X-ray contrast agents are shown in U.S. Pat. No. 5,447,711 and comprise iotrolan, ioxaglate, iodecimol, and iosarcol. Other suitable contrast agents are iotusal, ioxilane, and iofrotal.

In some embodiments of the present invention, the water soluble non-ionic X-ray contrast agent has a low osmomolality such as iohexol, iodixanol, ioversol, iopamidol, and iotrolane.

For example, iohexol ($C_{19}H_{26}I_3N_3O_9$) as well as its dimer iodixanol, may be used as a water soluble non-ionic X-ray contrast agent. These substances do not influence bone formation and they have a good biocompatibility in bone.

Alternatively x-ray opacity of the implant may be achieved by addition of Barium Sulphate or some other non-water soluble contrast agent.

In other embodiments of the present invention x-ray opacity is achieved by incorporating non-demineralized or partially demineralized bone wherein the mineral components are naturally radiopaque. Synthetic materials such as hydroxyapatite, tricalcium phosphate, or similar materials may be incorporated into the graft.

Figure 2:
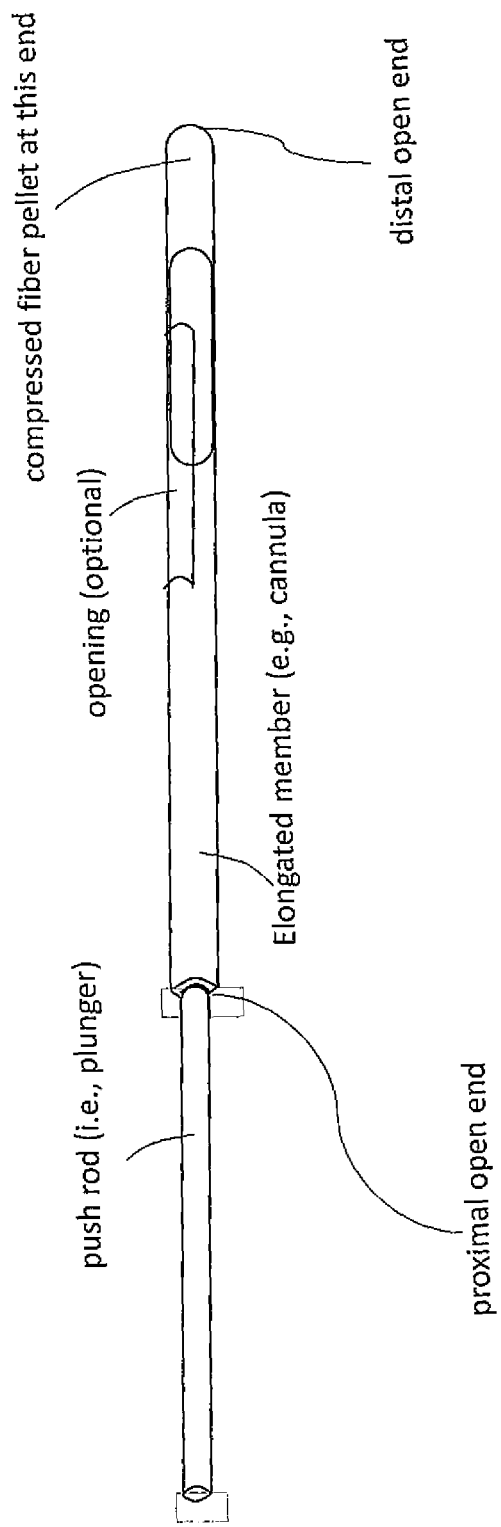
FIG. 2 shows a device for the delivery of a bone repair implant into a subject, according to embodiments of the present invention.

Introduction of an implant according to embodiments of the present invention into a patient is accomplished by placing the implant into the proximal end of an elongated member as shown in FIG. 2. The elongated member is placed into the patient through a minimal incision and the distal end of the tube is placed at the point where delivery of the implant is required. This may be confirmed by means of fluoroscopic imaging or other means. When the surgeon is satisfied that the positioning is correct the implant may be advanced down the tube and out into the patient by means of a plunger.

The delivery tube may be straight or curved. In the latter instance the plunger will be flexible, being made of nitinol wire or braided nitinol wire or other suitable material.

In some embodiments the implant will be sized exactly to the required implant size, for example, to fit into the cavity in an interbody fusion cage. Alternatively the required implant volume will require a number of discrete 'pellets' to facilitate delivery, or to allow for placement of graft at multiple locations within the surgical site.

Figure 1B:
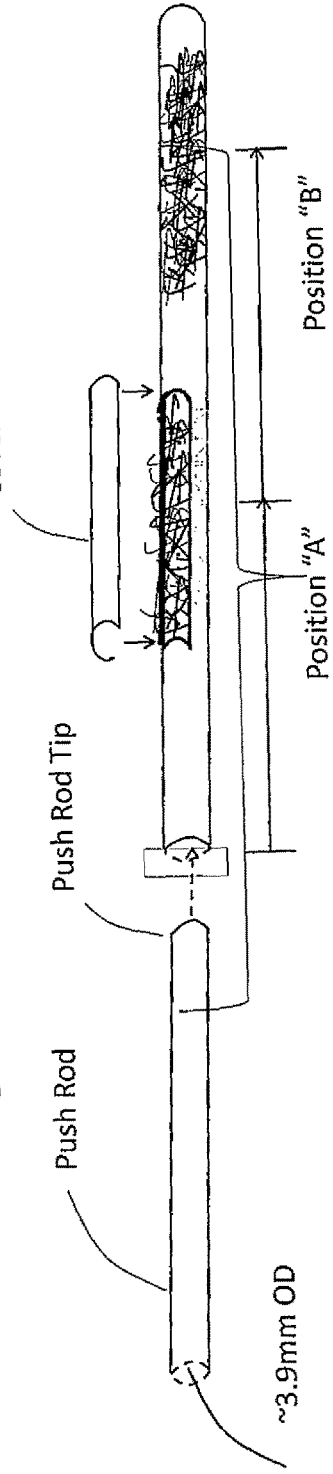
FIG. 1B shows a device for forming bone repair implants from bone fibers, according to embodiments of the present invention.
Figure 1C:
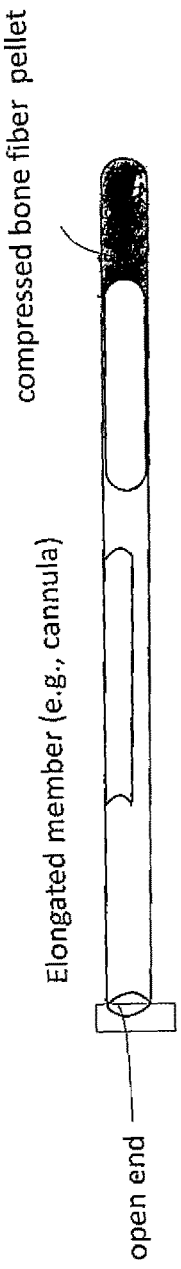
FIG. 1C shows a device for forming a bone repair implant, according to embodiments of the present invention.
Figure 1D:
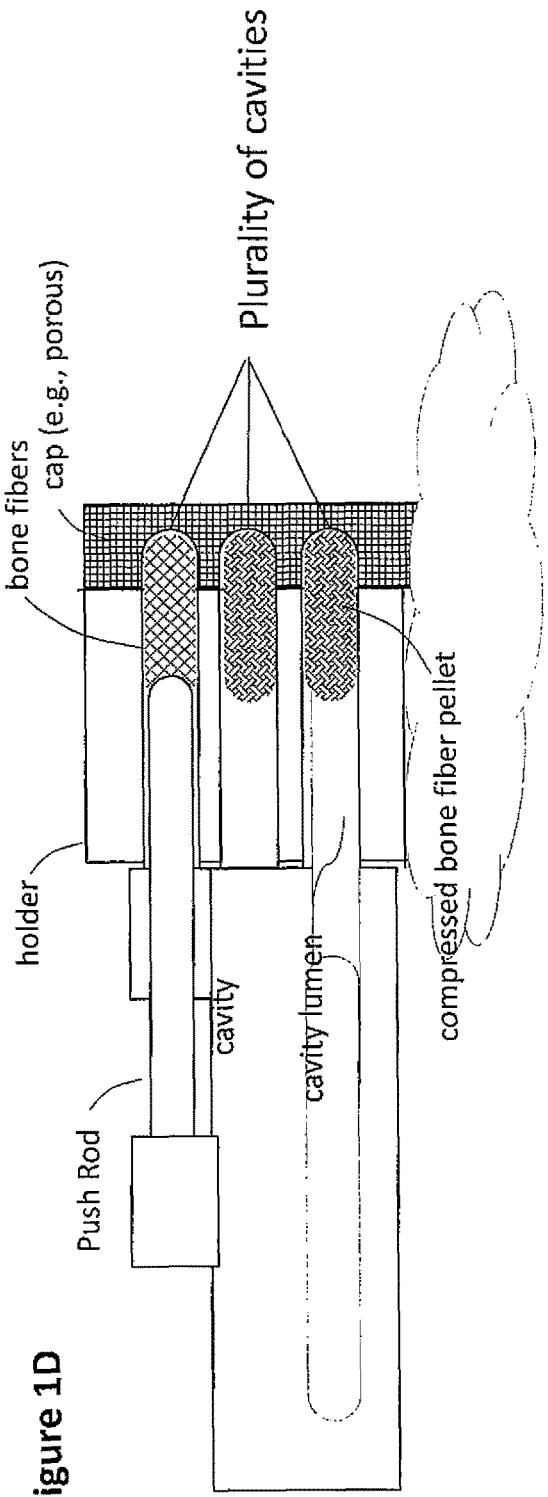
FIG. 1D shows a device for forming a plurality of bone repair implants, according to embodiments of the present invention.
Figure 1E:
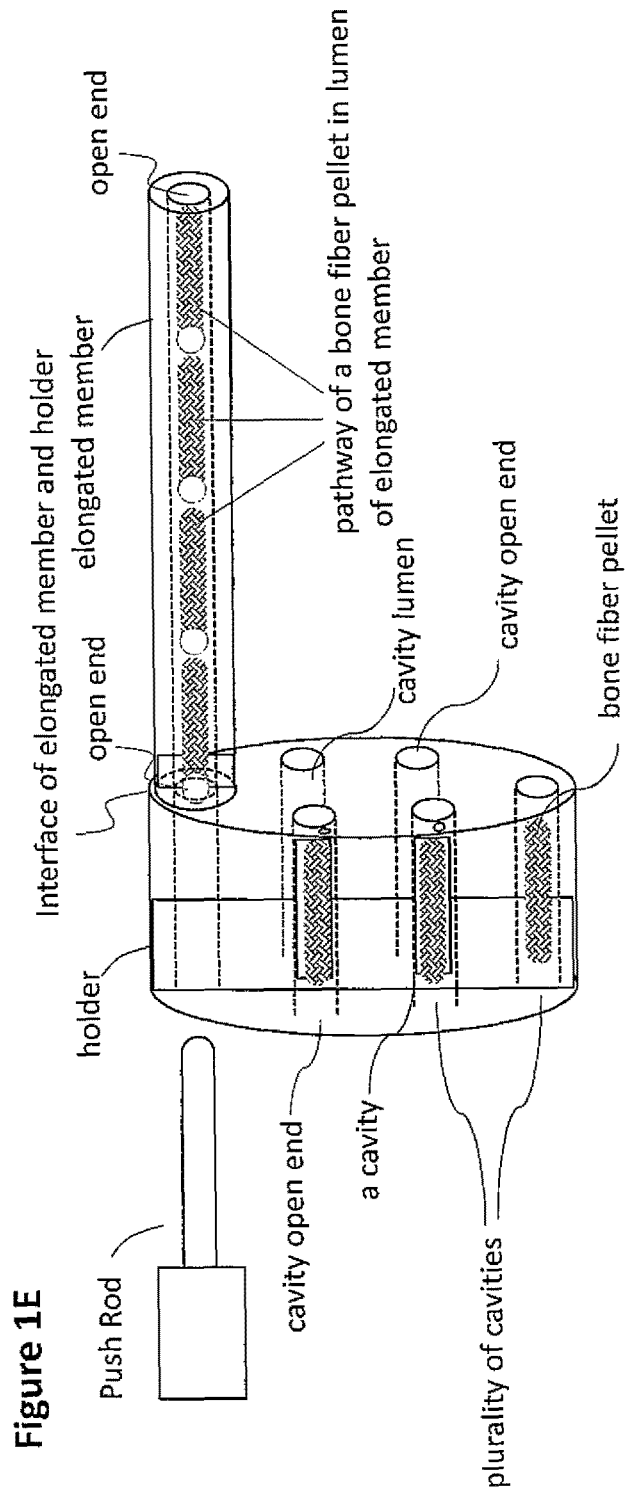
FIG. 1E shows a device for holding a plurality of bone repair implants, according to embodiments of the present invention.

The delivery tube may optionally have an additional cartridge holding a number of implants such as shown in FIG. 1D and FIG. 1E, that may be advanced into the delivery tube easily and implanted sequentially. The delivery tube may be "side loading" such that when the delivery plunger is retracted back past the cartridge an implant moves into the delivery tube. Forward movement of the plunger then moves the implant down the delivery tube and into the patient. The pellet may be advanced into the multiple cavity holder of FIG. 1D and compressed to a defined level to control the implant density by advancing the push rod to a set point (approximately 1.5-2.5 cm from the end). A holder cap may be deployed to stop the pellet from being expelled, and may be later removed and interfaced to a cannula as shown in FIG. 1E to allow implant delivery. The DBF pellet may be shaped with a convex proximal end and concave distal end by the push rod. Alternatively implants may be introduced by separate means into the end of the delivery tube. Implants having a pellet shape are easier to introduce into delivery tubes.

In some embodiments of a holder introduction system as shown in FIG. 1E, the pellets, which may be pellet-shaped, are loaded into the holder. For example 6 pellets may be loaded in a 6-chamber (6-cavity) holder. The holder with pellets inside may be placed into an oven and heated to between 40° C. and 70° C. for a period of 1-60 minutes or more.

In some embodiments the mass and thermal transfer properties of the holder and its components, as well as the oven type and temperature may be controlled to impart the correct properties on the pellets.

In some embodiments the surface smoothness and materials of the holder and holder cavities may be selected to further control the pellets surface lubricity.

In some embodiments implants are formed and stored in tubes. To facilitate loading into the end of the delivery tube a recess is formed in the end of the elongated member (e.g., cannula) to hold the storage tube in correct alignment.

In some embodiments a plurality of implants are stored in a holder that is configured to attach to a delivery tube to allow easy deployment of multiple implants. Alternatively the delivery device may be loaded with multiple implants at the time of surgery.

At the time of surgery, prior to implantation, a small amount of a water soluble contrast agent such as Iopam idol may be injected into the implant to provide visualization during implantation.

EXAMPLES

The following examples use cortical bovine (cow) bone. As discussed herein, either human or animal bone may be used as a source of cortical bone. Fibers were produced using the methodology described in patent application US 2014/0314822.

Example 1

Bone Fiber Pellets. Bone fiber pellets were formed by placing wet fibers into a tube with a window opening which could be opened to act as a "hopper" for loading DBF as shown in FIG. 1A. The cover was then closed and the DBF was formed into the diameter of the tube (4.1 mm). The cover may be removed, or the cover may be moveable from a first position to a second position. The plunger was advanced from Position "A" to Position "B" as shown in FIG. 1B to compress the fibers and form them into the required shape as shown in FIG. 1C. Pellets were then heated at 45° C. and 50° C. for 10 minutes. Following heat treatment the pellets were dried in a vacuum oven set at 25° C. with an air flow of 0.5 liter per minute. Additional samples were not heat treated.

Example 2

Minimally Invasive Delivery. Pellets from Example 1 were loaded individually into a delivery cannula, as shown in FIG. 2. The pellets could be easily ejected from the distal end by use of the plunger. Once ejected the pellets were placed in saline. All pellets swelled, with those heat treated swelling less rapidly, and remaining cohesive.

Example 3

Addition of Bone Marrow Aspirate. In a variant of Example 2, once loaded into the delivery device, bone marrow aspirate was introduced into a pellet by means of a syringe with needle placed in the center of the pellet. The pellet hydrated but was still able to be ejected from the delivery device.

Example 4

In one experiment DBF was prepared and then introduced into MIS cannulae of varying internal diameter. Cannulae sizes ranged from 2.0 mm to 5.5 mm. The process was able to work for all of these sizes and the size range could be extended above 5.5 mm if required. Once the DBF was in the tube the rod was inserted and advanced. The hole on the end was held closed and the rod used to firmly compact the graft. Additional graft was then introduced and this process repeated. This serial introduction is optional, but adds utility by creating discrete pellets rather than one long graft allowing for ease of placement into various regions of the graft site. In this experiment three 0.25 gm pellets were formed in the small cannula and three 0.5 gm pellets in the large cannula. The pellets were easily individually expelled. After expelling the pellets they were placed into water and immediately absorbed water and then began to swell.

Example 5

DBF fibers as previously described were divided into 0.5 gm quantities. The fibers were rolled between fingers to mimic the use of rollers, and they became more entangled and cohesive. Rolling of DBF fibers into a cylindrical or other shape appears to enhance entanglement of the fibers and improve integrity and coherence of the fiber mass. It also facilitates handling and packing of the fibers into a hopper minimizes fibers being caught or hung up on the apparatus. Rolled DBF could then be placed into the slot of the device shown in FIG. 1B. After tucking the fibers into place the cover was held firmly over the graft loading hatch and then the plunger advanced to force the graft into the cannula. A tamping motion was found to work well. The graft was then advanced to the end of the tube which was occluded so compression could be applied to the pellet. Pellets were then heated for various time and temperatures.

Example 6

A thin walled tube with inner wall diameter matching closely to a delivery cannula was modified to have a 'hatch' as previously described. The thin walled tube fitted into an alignment recess in the delivery cannula making coupling and graft introduction easier. 0.5 gm of DBF was packed into the holder, the hatch held securely closed and the pellet advanced into the tube. The resulting pellet was about 1 inch long. Heated and unheated pellets were then introduced from the production tube to the delivery cannula by aligning the tube in the cannula recess and simply advancing the push rod. Pellets were easily transferred to the cannula.

Example 7

Samples were made using the thin walled 4.1 mm ID (inner diameter) tube and employing: (a) no heat, (b) 5 min at 45 deg C., and (c) 10 minutes at 45 deg C. These were deployed satisfactorily.

While embodiments of the present invention have been illustrated and described with reference to certain exemplary embodiments, those of ordinary skill in the art will understand that various modifications and changes may be made to the described embodiments without departing from the spirit and scope of the present invention, as defined in the following claims. Additionally, although relative terms such as "outer," "inner," "upper," "lower," "below," "above," "vertical, "horizontal" and similar terms have been used herein to describe a spatial relationship of one element to another, it is understood that these terms are intended to encompass different orientations of the various elements and components of the device in addition to the orientation depicted in the figures.

An Embodiment 1 is a bone repair composition including a plurality of fibers cut from demineralized bone in a form of a pellet, the pellet having an outermost layer of bone fibers which are annealed.

An Embodiment 2 includes the bone repair composition of Embodiment 1, wherein the outermost layer of bone fibers may be annealed by heating and/or dehydrothermal treatment.

An Embodiment 3 includes the bone repair composition of Embodiment 1, wherein the outermost layer of bone fibers are annealed by chemically combining a hydroxy group from a functional group of a collagen molecule of the outermost layer of bone fibers and a hydrogen ion from a functional group of another collagen molecule of the outermost layer of bone fibers.

An Embodiment 4 includes the bone repair composition of Embodiment 1, wherein the outermost layer of bone fibers are annealed by heating the bone fibers in a metallic mold.

An Embodiment 5 includes the metallic mold of Embodiment 4, wherein the mold is stainless steel.

An Embodiment 6 includes a method of making a bone repair composition for minimally invasive surgery includes demineralizing cortical bone to form demineralized bone, repeatedly cutting the demineralized bone to form a plurality of bone fibers, and adding the plurality of bone fibers to a mold to form a mold of bone fibers.

An Embodiment 7 includes the method of Embodiment 6, wherein the mold includes an elongated member, the method further includes compressing the bone fibers in the elongated member to form a pellet of bone fibers.

An Embodiment 8 includes the method of Embodiment 6, the method further including heating the mold to form a mold of bone fibers having an annealed outermost layer.

An Embodiment 9 includes the method of Embodiment 8, wherein the mold is metallic.

An Embodiment 10 includes the method of Embodiment 8, wherein the mold is thermally conductive.

An Embodiment 11 includes the method of Embodiment 8, wherein the mold includes stainless steel.

An Embodiment 12 includes a device for forming a bone repair composition, including an elongated member having a lumen extending therethrough between a first open end to a second open end, the lumen configured to receive bone fibers, a removable cap configured to be positioned on the second open end, and a push rod receivable through the first open end of the elongated member and into the lumen toward the second open end, the push rod configured to compress the bone fibers in the lumen against the removable cap to form a pellet.

An Embodiment 13 includes the device of Embodiment 12, wherein the removable cap is configured with a recessed formation configured to provide the pellet with an atraumatic end.

An Embodiment 14 includes the device of Embodiment 12, wherein the elongated member has a side wall with an opening providing communication between the lumen and outside of the elongated member through which the bone fibers may be placed in the lumen.

An Embodiment 15 includes the device of Embodiment 14, wherein the opening is positioned closer to the second open end than to the first open end.

An Embodiment 16 includes the device of Embodiment 14, further including a removable cover adapted to cover the opening.

An Embodiment 17 includes the device of Embodiment 12, wherein the removable cap is porous.

An Embodiment 18 includes the device of Embodiment 12, wherein the push rod has a length greater than a length of the elongated member.

An Embodiment 19 includes the device of Embodiment 12, wherein the lumen is metallic.

An Embodiment 20 includes the device of Embodiment 12, wherein the lumen comprises stainless steel.

An Embodiment 21 includes the device of Embodiment 12, wherein the push rod is made of metal or plastic.

An Embodiment 22 includes the device of Embodiment 12, wherein the push rod includes stainless steel.

An Embodiment 23 includes the device of Embodiment 12, wherein the elongated member is straight or curved and the push rod is rigid or flexible.

An Embodiment 24 includes the device of Embodiment 12, wherein the elongated member is curved and the push rod is flexible.

An Embodiment 25 includes the device of Embodiment 12, further comprising bone fibers.

An Embodiment 26 includes a device for forming a plurality of bone repair compositions, including a holder comprising a plurality of cavities, each cavity having a cavity lumen extending therethrough between a first open cavity end and a second open cavity end, and a removable cavity cap having a recess configured to close the second open cavity end, the lumen configured to receive bone fibers, a removable cap configured to be positioned on at least one of the plurality of second open cavity ends, and a push rod receivable through each of the first open cavity ends of the plurality of cavities and into the cavity lumen toward the second cavity open end, the push rod configured to compress the bone fibers in the cavity lumen against the removable cap to form a pellet.

An Embodiment 27 includes the device of Embodiment 26, wherein the removable cap is porous.

An Embodiment 28 includes the device of Embodiment 26, wherein the plurality of cavities are metallic.

An Embodiment 29 includes a device for holding a plurality of bone fiber pellets, including a holder including a plurality of cavities, each cavity having a cavity lumen extending therethrough between a first open cavity end and a second open cavity end, the cavity lumen configured to receive a bone fiber pellet, and a removable cap configured to be positioned on at least one of the plurality of second open cavity ends.

An Embodiment 30 includes the device of Embodiment 29, wherein the holder is adapted to attach to a bone delivery device.

An Embodiment 31 includes an apparatus for minimally invasive delivery of a bone repair composition to a subject, the apparatus, including an elongated member having a lumen extending therethrough between a first open end to a second open end, the lumen configured to receive a bone fiber pellet, and a push rod receivable through the first open end of the elongated member and into the lumen toward the second open end, the push rod configured to advance the bone fiber pellet out of the lumen and into the subject.

An Embodiment 32 includes the apparatus of Embodiment 31, wherein the elongated member is straight or curved and the push rod is rigid or flexible.

An Embodiment 33 includes the apparatus of Embodiment 31, further including a holder including a plurality of cavities, each cavity having a cavity lumen extending therethrough between a first open cavity end and a second open cavity end, each lumen configured to receive a bone fiber pellet, wherein the holder is adapted to attach to the elongated member and align the lumen of the elongated member with one of the cavity lumens.

An Embodiment 34 includes the apparatus of Embodiment 31 or Embodiment 33, further including a bone fiber pellet.

An Embodiment 35 includes a method of delivering a bone repair composition to a subject by minimally invasive surgery, the method includes using the apparatus of Embodiment 34.

An Embodiment 36 includes the method of Embodiment 35, wherein the bone fiber pellet includes a contrast agent.

The invention claimed is:

1. A device for delivering one or more bone fiber pellets to one or more target sites, comprising:
 a holder with a plurality of cavities each having a cavity lumen extending therethrough between a first open end to a second open end, the cavity lumen configured to receive a bone fiber pellet;
 an elongated member forming a delivery tube positioned at an interface of the holder and the elongated member at the second open end of one of the cavity lumens, the delivery tube between a first tube open end aligned with the second open end of one of the cavity lumens and a second tube open end; and
 a push rod receivable through the first open end corresponding to the cavity lumen positioned at the interface of the holder and the elongated member, the push rod configured to push the bone fiber pellet into the delivery tube and out of the device to the one or more target sites.

2. The device of claim 1, further comprising a removable cap for covering the second tube open end.

3. The device of claim 1, wherein the push rod has a length greater than a length of the elongated member.

4. The device of claim 1, wherein the cavity lumens are metallic.

5. The device of claim 1, further comprising one or more bone fiber pellets.

6. The device of claim 1, wherein the plurality of cavities includes up to 6 cavities.

* * * * *